US011134991B2

United States Patent
Biedermann et al.

(10) Patent No.: US 11,134,991 B2
(45) Date of Patent: Oct. 5, 2021

(54) STABILIZATION DEVICE FOR BONES OR VERTEBRAE

(71) Applicant: BIEDERMANN TECHNOLOGIES GMBH & CO. KG, Donaueschingen (DE)

(72) Inventors: Timo Biedermann, Trossingen (DE); Wilfried Matthis, Weisweil (DE); Kevin Dold, Geislingen (DE)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 0 days.

(21) Appl. No.: 16/050,753

(22) Filed: Jul. 31, 2018

(65) Prior Publication Data
US 2019/0038319 A1 Feb. 7, 2019

Related U.S. Application Data

(60) Provisional application No. 62/541,012, filed on Aug. 3, 2017.

(30) Foreign Application Priority Data

Aug. 3, 2017 (EP) .................................... 17184814

(51) Int. Cl.
*A61B 17/70* (2006.01)
(52) U.S. Cl.
CPC ........ *A61B 17/7032* (2013.01); *A61B 17/701* (2013.01); *A61B 17/7037* (2013.01)
(58) Field of Classification Search
CPC .. A61B 17/7002–7031; A61B 17/7032; A61B 17/7037
See application file for complete search history.

(56) References Cited

U.S. PATENT DOCUMENTS 8,257,399 B2 * 9/2012 Biedermann ...... A61B 17/7032
606/265
8,979,905 B2 3/2015 Butler
(Continued)

FOREIGN PATENT DOCUMENTS

| EP | 1 857 065 A1 | 11/2007 |
| WO | WO 2007/087476 A1 | 8/2007 |
| WO | WO 2011/006267 A1 | 1/2011 |

OTHER PUBLICATIONS

Extended European Search Report for Application No. 17184814.6, dated Feb. 6, 2018, 8 pages.

*Primary Examiner* — Nicholas J Plionis
(74) *Attorney, Agent, or Firm* — Lewis Roca Rothgerber Christie LLP

(57) ABSTRACT

A stabilization device for bones or vertebrae includes a rod having a rod axis and a plurality of distinct external surfaces that extend parallel to the rod axis, such that for a cross-section of the rod, the distinct external surfaces are arranged at respective angles relative to one another around the rod axis, a bone anchoring device including a receiving part having a channel for receiving the rod and a contact surface for supporting the rod, and a fixation member with a contact surface for fixing the rod in the channel. When the rod is fixed in the channel with the fixation member, the contact surfaces of the receiving part and the fixation member together form surface portions that are shaped to correspond to at least three of the distinct external surfaces, such that the rod is clamped along the at least three distinct external surfaces.

21 Claims, 11 Drawing Sheets

(56) References Cited

U.S. PATENT DOCUMENTS

| | | | |
|---|---|---|---|
| 2007/0191841 A1* | 8/2007 | Justis | A61B 17/701 606/250 |
| 2007/0270819 A1* | 11/2007 | Justis | A61B 17/701 606/279 |
| 2008/0051780 A1* | 2/2008 | Vaidya | A61B 17/7035 606/86 A |
| 2008/0086130 A1 | 4/2008 | Lake et al. | |
| 2008/0177318 A1* | 7/2008 | Veldman | A61B 17/7005 606/256 |
| 2010/0063544 A1* | 3/2010 | Butler | A61B 17/701 606/261 |
| 2010/0160976 A1* | 6/2010 | Biedermann | A61B 17/7035 606/302 |
| 2011/0276098 A1* | 11/2011 | Biedermann | A61B 17/7037 606/305 |
| 2012/0123480 A1* | 5/2012 | Freudiger | A61B 17/701 606/278 |
| 2012/0179209 A1* | 7/2012 | Biedermann | A61B 17/7037 606/305 |
| 2013/0085536 A1* | 4/2013 | Biedermann | A61B 17/7035 606/308 |
| 2014/0350602 A1* | 11/2014 | Seme | A61B 17/70 606/250 |
| 2017/0020574 A1* | 1/2017 | Biedermann | A61B 17/7076 |

* cited by examiner

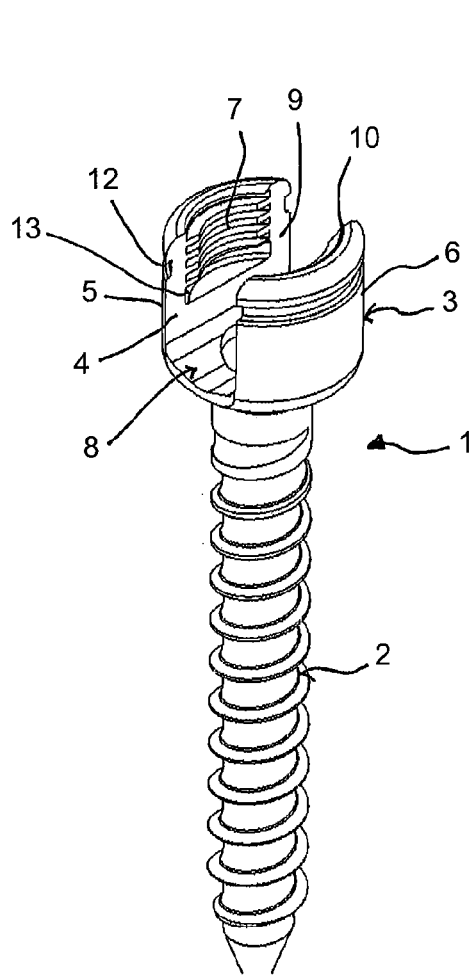
Fig. 3
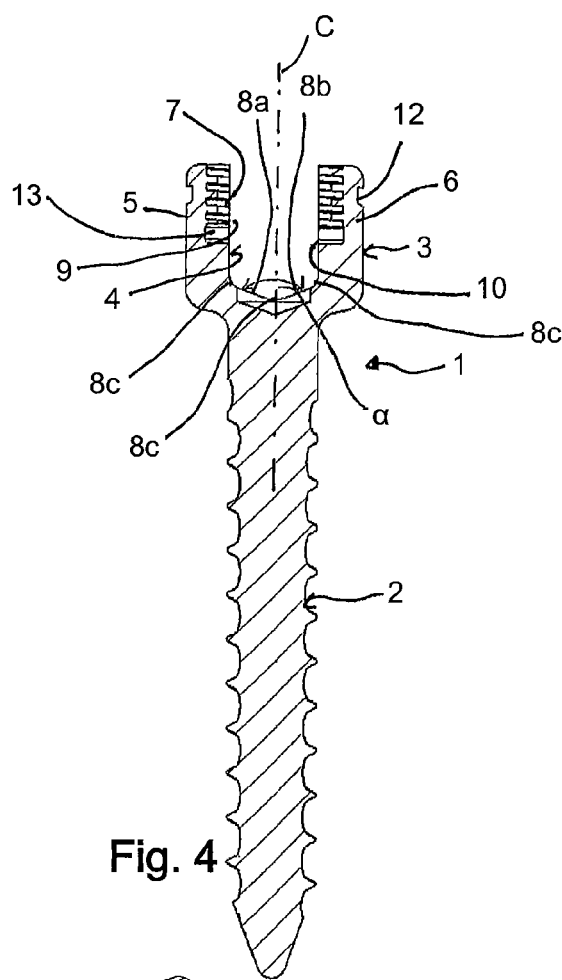
Fig. 4
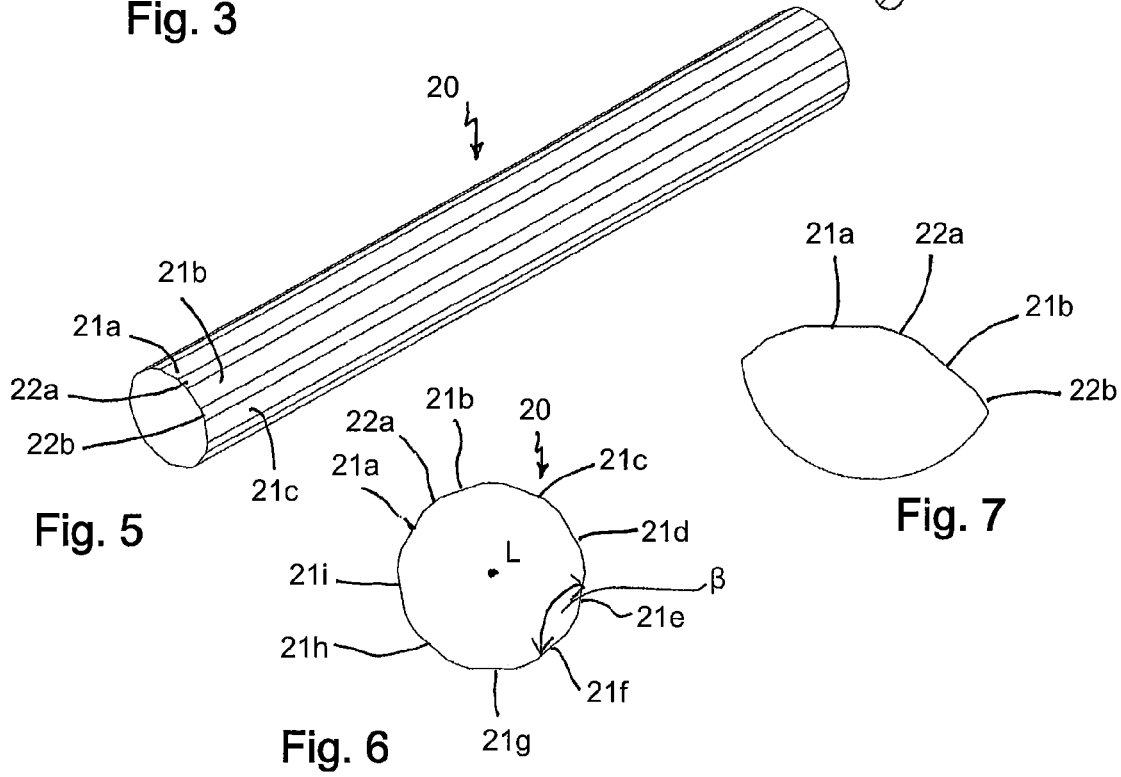
Fig. 5
Fig. 6
Fig. 7

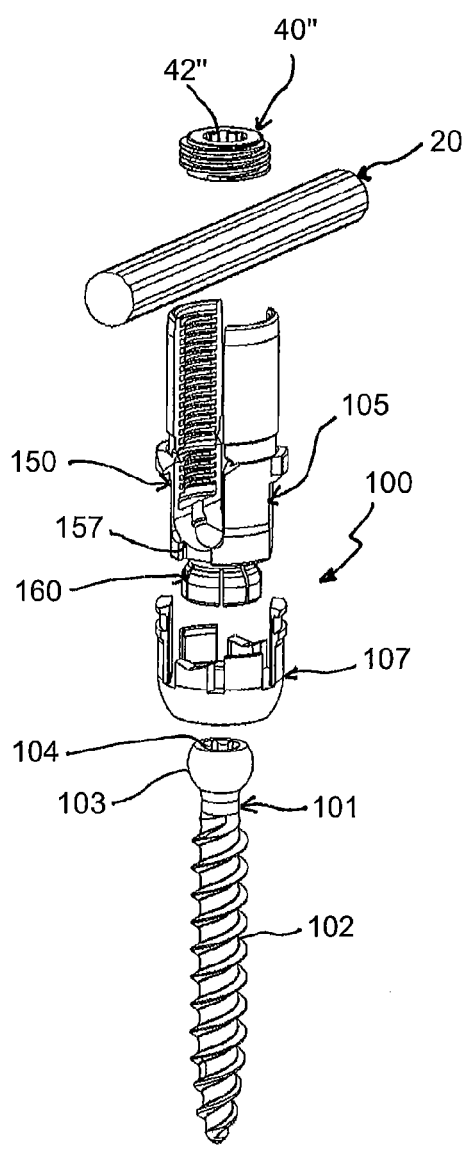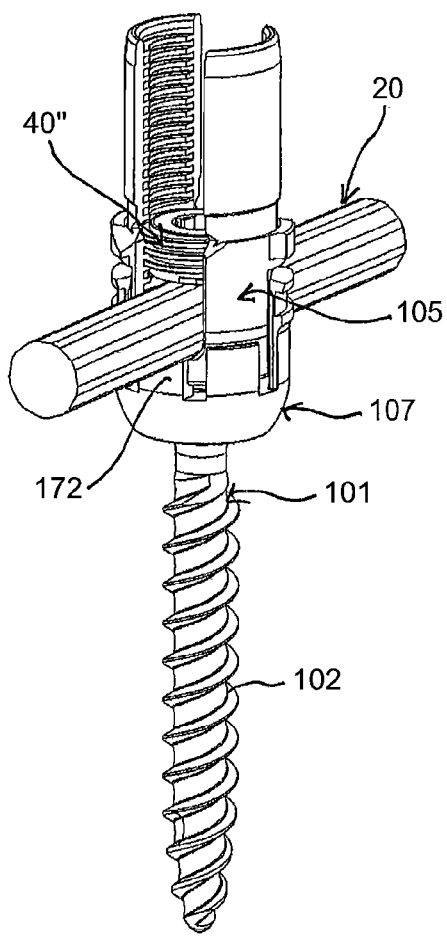
Fig. 23
Fig. 24

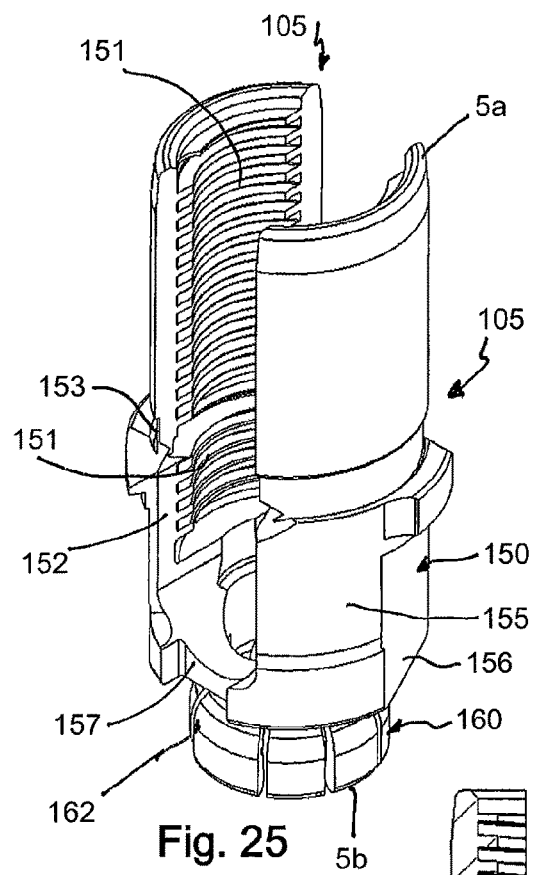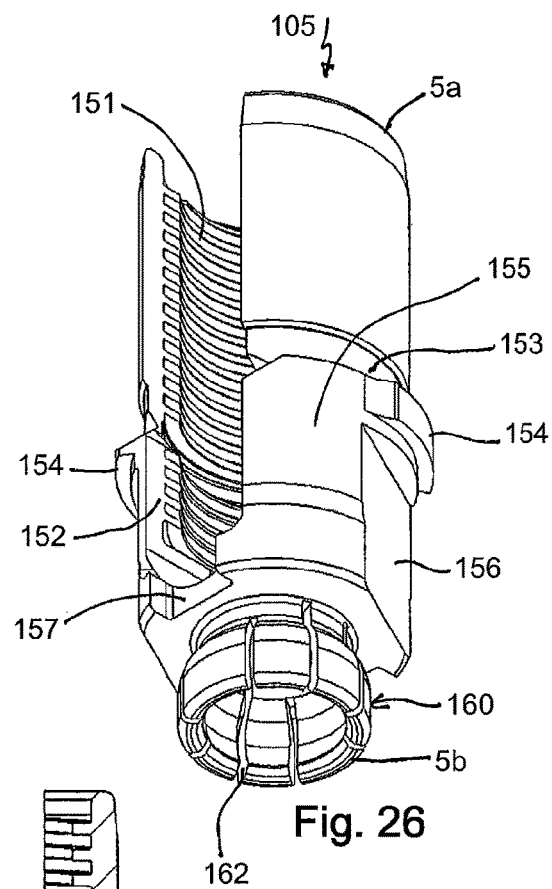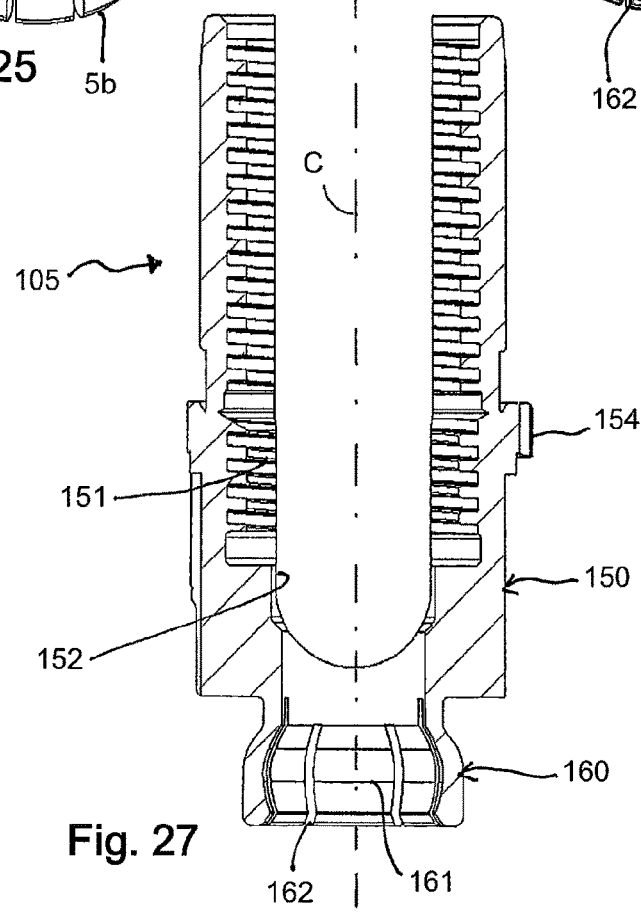

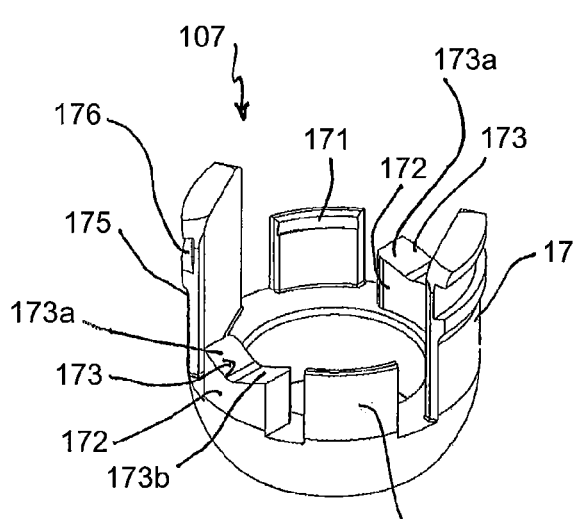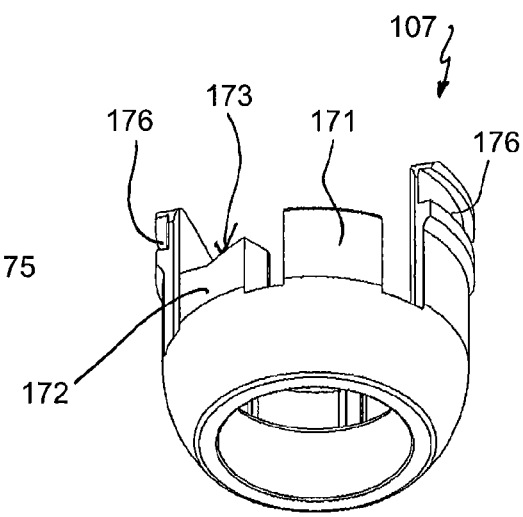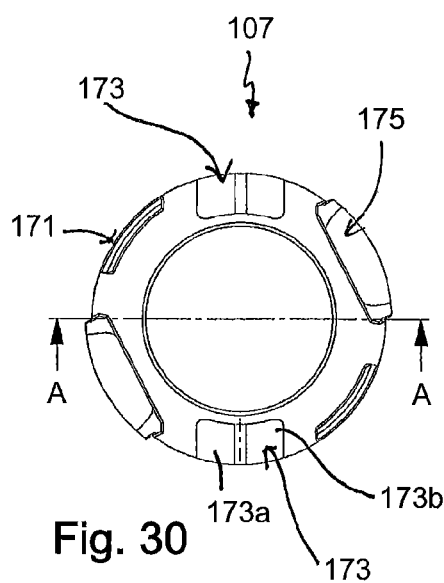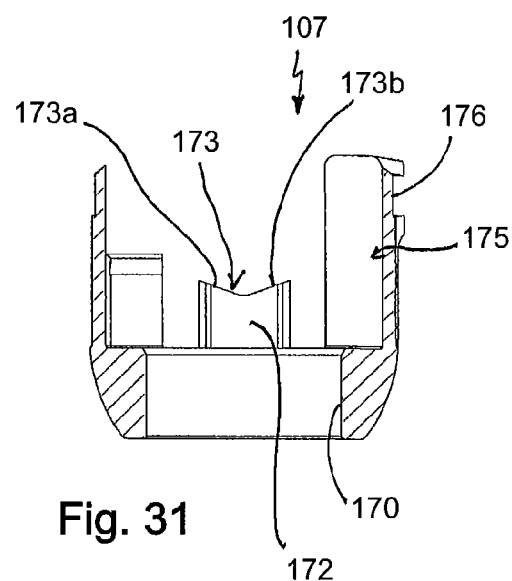

STABILIZATION DEVICE FOR BONES OR VERTEBRAE

CROSS-REFERENCE TO RELATED APPLICATION(S)

The present application claims priority to and the benefit of U.S. Provisional Patent Application No. 62/541,012, filed Aug. 3, 2017, the contents of which are hereby incorporated by reference in their entirety, and claims priority from European Patent Application EP 17 184 814.6, filed Aug. 3, 2017, the contents of which are hereby incorporated by reference in their entirety.

BACKGROUND

The invention relates to a stabilization device for bones or vertebrae, more particularly to a device for stabilizing the spinal column that includes a rod and a receiving part of a bone anchor that is adapted to the shape of the rod.

DESCRIPTION OF RELATED ART

U.S. Pat. No. 8,257,399 describes an anchoring device for anchoring a rod in bone or in a vertebra for use with at least two rods having different diameters. The bone anchoring device includes a receiving part with a base for receiving the rod and a fixation member for fixing the rod in the receiving part. The fixation member and the base each has a contact surface shaped such that the rod is clamped along three contact lines.

SUMMARY

In the treatment of multi-segmental deformities of the spine using long rods, corrections may become necessary that involve limited rotational movements of a vertebra around the rod axis. During such correction steps the rod axis may be used as an axis of rotation. Hence, rotational forces act onto the rod that has been clamped in the receiving part of a bone anchoring device. When a rod having a circular cross-section is used, the receiving part may unintentionally slip or rotate around the rod axis.

It is an object of the invention to provide a stabilization device for bones or vertebrae that provides for improved handling combined with long-term security.

According to an aspect of the invention, the rod of the stabilization device has at least a rod portion with a rod axis and with an n number of distinct external surfaces that are arranged in an n-fold rotationally symmetrical manner around the rod axis. Further, a rod support of a receiving part of the bone anchoring device and a fixation member each includes at least one contact surface that is configured to contact one of the external surfaces of the rod, wherein said contact surfaces and said external surfaces are configured and arranged to clamp the rod along at least three surface areas of the rod. Thereby, a form-fit connection between the rod and the receiving part is achieved. Compared to a rod with a circular cross-section, the risk of slipping of the rod in the receiving part around the rod axis may be reduced. As a consequence, higher forces in a rotational direction may be applied. This better permits performing of correction steps that involve rotating a vertebra in a limited manner around the rod axis.

Moreover, due to the n-fold rotational symmetry of the rod, the rod can be rotated relative to the receiving part and fixed every time when an external surface of the rod cooperates with the contact surface of the base and the fixation member.

In a further aspect of the invention, two or more contact surfaces are provided at the fixation member. Thereby the resistance against slipping of the receiving part relative to the rod can be further increased.

BRIEF DESCRIPTION OF THE DRAWINGS

Further features and advantages will become apparent from the description of embodiments by means of the accompanying drawings. In the drawings:

FIG. 3 shows a perspective view of a bone anchoring device of the stabilization device according to FIGS. 1 and 2.

FIG. 4 shows a cross-sectional view of the bone anchoring device of FIG. 3, the cross-section taken in a plane including the anchor axis and extending through centers of legs of a receiving part of the bone anchoring device.

FIG. 5 shows a perspective view of a rod of the stabilization device according to FIGS. 1 and 2.

FIG. 6 shows a front view perpendicular to a rod axis of the rod of FIG. 5.

FIG. 7 shows an enlarged portion of FIG. 6.

FIG. 23 shows a perspective exploded view of a third embodiment of the stabilization device.

FIG. 24 shows a perspective view of the stabilization device of FIG. 23 in an assembled state.

FIG. 25 shows a perspective view from the top of a receiving part of the stabilization device according to FIGS. 23 and 24.

FIG. 26 shows a perspective view from the bottom of the receiving part of the stabilization device according to FIGS. 23 and 24.

FIG. 27 shows a cross-sectional view of the receiving part shown in FIGS. 25 and 26, the cross-section taken in a plane including a central axis of the receiving part and extending through centers of legs of the receiving part.

FIG. 28 shows a perspective view from the top of a locking ring of the stabilization device shown in FIGS. 23 and 24.

FIG. 29 shows a perspective view from the bottom of the locking ring shown in FIG. 28.

FIG. 30 shows a top view of the locking ring shown in FIGS. 28 and 29.

FIG. 31 shows a cross-sectional view of the locking ring along line A-A in FIG. 30.

DETAILED DESCRIPTION

Figure 1:
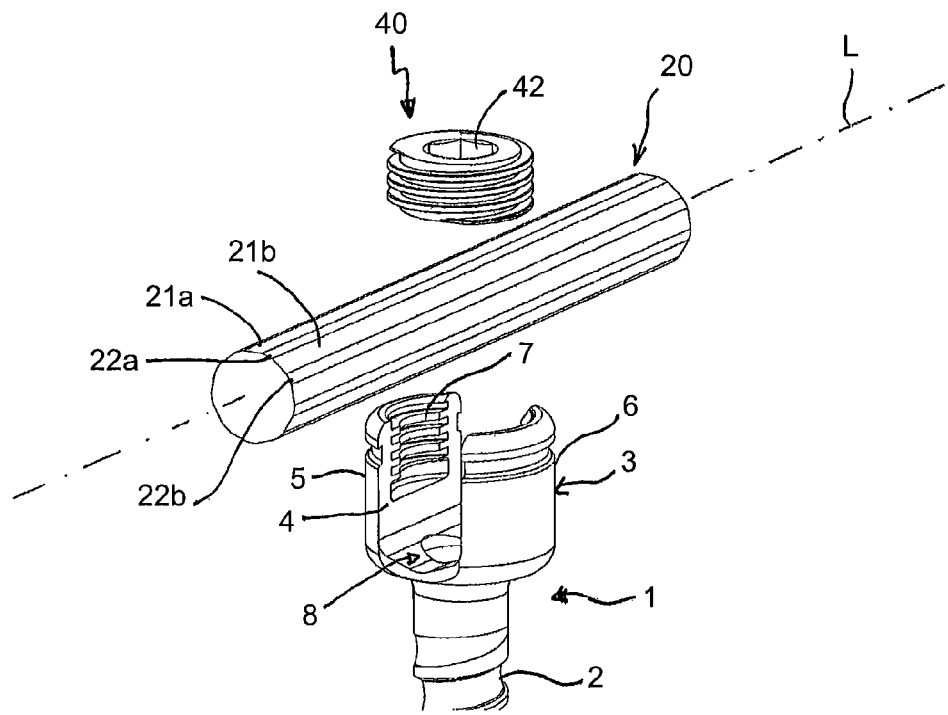
FIG. 1 shows a perspective exploded view of a stabilization device according to a first embodiment.
Figure 2:
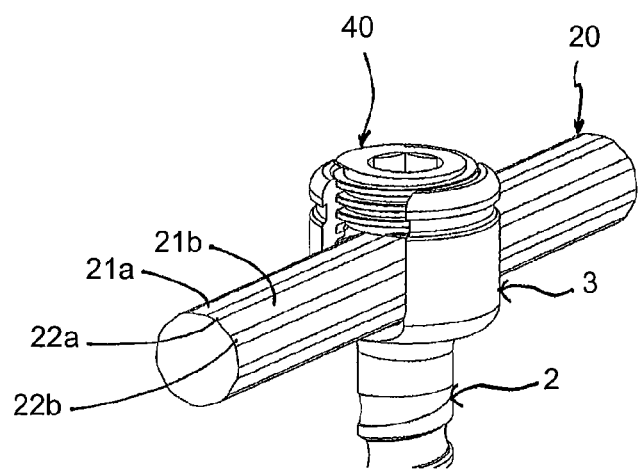
FIG. 2 shows the stabilization device of FIG. 1 in an assembled state.

A stabilization device according to a first embodiment is described with reference to FIGS. 1 to 11. The stabilization device includes a bone anchoring device 1, a stabilization member in the form of a rod 20, and a fixation member 40. The bone anchoring device 1 includes a shank 2 that has a bone thread on at least a portion thereof. At one end of the shank 2 a receiving part 3 for receiving the rod 20 is formed. The receiving part 3 is designed as a substantially cylindrical part that is fixedly connected to one end of the shank 2 to form a so-called monoaxial bone anchor. At the side of the receiving part 3 opposite to the shank 2, a recess 4 forming two free legs 5, 6 is provided by means of which a channel for receiving the rod 20 is defined. A coaxial bore 7 extends from a free end of the legs 5, 6 to a distance from the free end. The coaxial bore 7 is at least partially threaded for permitting the fixation member 40 to be screwed into the bore.

Figure 11:
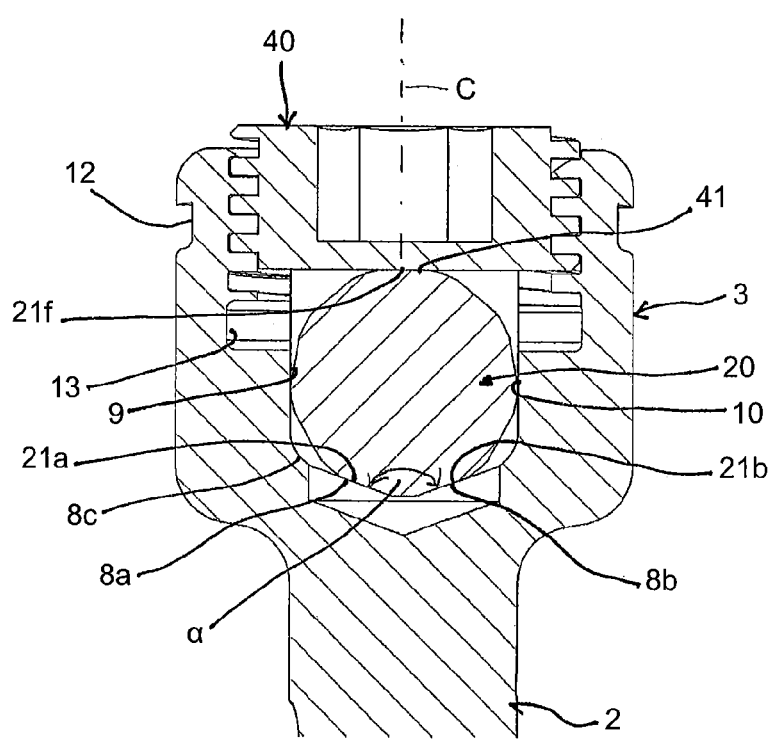
FIG. 11 shows a cross-sectional view of the stabilization device of FIGS. 1 and 2, the cross-section taken in a plane perpendicular to the rod axis.

As depicted in more detail in FIGS. 3, 4 and 11, the channel formed by the legs 5, 6 includes a base 8 and two opposite sidewalls 9, 10. The sidewalls 9, 10 are substantially flat and extend in a substantially vertical direction, i.e. substantially parallel to the shank axis or central axis C of the receiving part 3. The distance between the sidewalls 9, 10, and hence, the width of the channel is slightly larger than the largest outer diameter of the rod 20 to be accommodated in the recess 4, so that the rod 20 can be inserted and guided therein, for example, in the direction of the rod axis L. The base 8 of the recess 4 has a substantially V-shaped cross-section. By the V-shape, two flat contact surfaces 8a, 8b are provided that form an angle α with each other. The angle α is preferably adapted to the shape of the rod 20 as described below. Specifically, the angle α may be an obtuse angle, i.e., it is greater than 90° and smaller than 180°. Between the flat contact surfaces 8a, 8b, and between each flat contact surface 8a, 8b and the respective adjacent sidewall 9, 10, transition portions 8c may be present that may be rounded or may be flat. Furthermore, in the center of the channel, a coaxial bore 11 may be formed.

On an outer surface of the legs 5, 6 of the receiving part, a circumferentially extending groove 12 for engaging with an instrument for performing surgical steps may be provided. Furthermore, an undercut 13 may be formed below the thread of the coaxial bore 7, as shown in FIGS. 3, 4, and 11.

Turning now to FIGS. 1, 2, and 5 to 7, the rod 20 is straight and has a rod axis L. A plurality of n flat external surfaces $21a$, $21b$, ..., $21i$ are formed on the outside of the rod 20. More specifically, in a cross-sectional view, the flat external surfaces lie on the sides of a regular polygon. The inside of the rod can be solid. The external surfaces $21a$, $21b$, ..., $21i$ extend along the whole length of the rod 20 and are spaced apart from each other in a circumferential direction at regular distances. Between the flat external surfaces $21a$, $21b$, ..., $21i$, intermediate surfaces $22a$, $22b$, ..., $22i$ are formed. The width of the intermediate surfaces $22a$, $22b$, ..., $22i$ in a circumferential direction may be smaller than the width of the external flat surfaces $21a$, $21b$, ..., $21i$, for example, it may be half or less of the width of the external surfaces $21a$, $21b$, ..., $21i$. The intermediate surfaces may be cylindrical or may be flat. A cylindrical shape may have an advantage in view of easier rotation of the rod relative to the receiving part 3. In total, there is an equal number n of intermediate surfaces compared to the number n of flat external surfaces.

The number n of the flat external surfaces $21a$, $21b$, ..., $21i$ is preferably greater than 3, more preferably an uneven number, and still more preferably an uneven number greater than 5. In the embodiment shown, 9 flat external surfaces are provided. The latter has been found to be suitable for a rod having a largest outer diameter between around 5 mm and around 7 mm. More in detail, as shown in FIG. 6, the rod 20 has a rotationally symmetrical cross-section in a plane perpendicular to the rod axis L, with respect to rotation of the rod around the rod axis L by distinct angles. Hence, the cross-section of the rod is n-fold rotationally symmetrical around a center point of the cross-sectional plane.

The angle β that is formed inside the rod by two consecutive external surfaces $21a$, $21b$, ..., $21i$ corresponds to the angle α of the base 8. Therefore, when the rod 20 is placed into the channel and rests on the base 8, two of the external surfaces $21a$, $21b$, ..., $21i$ contact the contact surfaces 8a, 8b of the base 8, as shown in FIG. 11. Thereby, a contact between the rod 20 and the base 8 is established at two surface areas. The surface area of the contact exceeds that of a macroscopic line contact that may be achieved with a rod having a cylindrical cross-section. With n=9, the angle α and the angle β are 140°. In other words, rotating the rod on a rod support surface of the base 8 by 40° results in an identical clamping configuration. Since a maximum outer dimension of the rod is smaller than an inner width of the receiving part, the rod can be rotated with respect to the receiving part.

The rod may be manufactured by starting from a rod with a circular cross-section and treating the outer surface thereof by grinding or cutting to generate the flat external surfaces.

Figure 8:
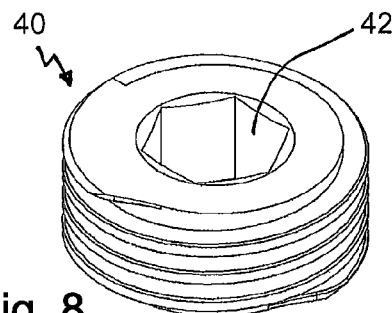
FIG. 8 shows a perspective view from the top of a fixation member of the stabilization device according to FIGS. 1 and 2.
Figure 9:
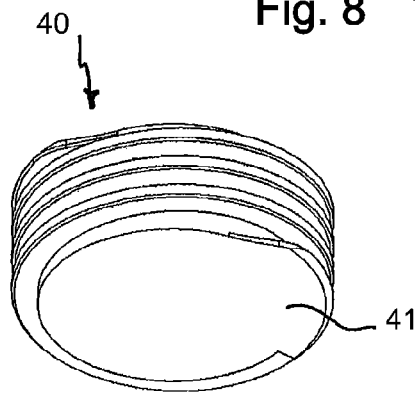
FIG. 9 shows a perspective view from the bottom of the fixation member of FIG. 8.
Figure 10:
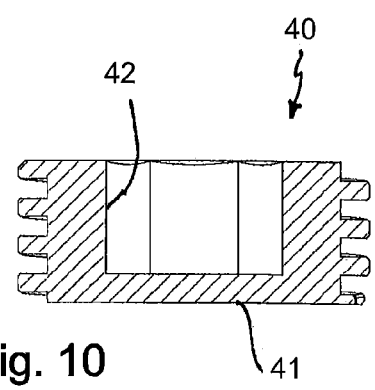
FIG. 10 shows a cross-sectional view of the fixation member of FIGS. 8 and 9.

As shown in FIGS. 8 to 10, the fixation member 40 is designed as a set screw that cooperates with the internal thread of the coaxial bore 7 of the legs 5, 6. At the lower side facing the rod 20, the fixation member 40 has a contact surface 41. The contact surface 41 is flat in at least a region of the whole surface area that is configured to touch the rod. Preferably the whole lower surface of the set screw is flat. At a side opposite to the contact surface 41, a recess 42 for engagement with a screwing-in tool is provided.

The fixation member 40 has such a length in an axial direction that when the fixation member 40 is screwed in between the legs 5, 6 and presses onto the inserted rod 20, the fixation member 40 projects only slightly or does not project out of the receiving part 3.

The bone anchoring device 1, the fixation member 40, and the rod 20 may be made of bio-compatible materials, for example, of titanium or stainless steel, of a bio-compatible alloy, such as a NiTi-alloy, for example Nitinol, of magnesium or magnesium alloys, or from a bio-compatible plastic material, such as, for example, polyether ether ketone (PEEK) or poly-1-lactide acid (PLLA). The parts can be made of the same or of different materials.

In use, at least two bone anchoring devices are inserted into a bone or a vertebra, and the rod 20 is inserted into the channel of each of the bone anchoring devices until it rests on the base 8 on the bottom of the receiving part 3. Since consecutive external surfaces 21a, 21b, ..., 21i include an angle β corresponding to the angle α of the V-shaped base 8 of the receiving part, when inserted, the rod 20 will assume a preferred position such that two adjacent external flat surfaces 21a, 21b, etc., contact the contact surfaces 8a, 8b of the V-shaped base 8.

As the number of external flat surfaces 21a, 21b, ..., 21i is uneven, there is an uppermost flat external surface 21f that is located on a side of the rod opposite to the V-shaped base 8 and that forms an uppermost portion of the rod 20. After the rod 20 has been placed onto the base 8, the fixation member 40 is inserted between the legs 5, 6 and screwed down until its contact surface 41 contacts the uppermost flat external surface 21f of the rod 20. Finally, the fixation member 40 is tightened. Thereby, the rod 20 is clamped in a form-fit manner at three surface areas, namely at two surface areas established by the contact of the contact surfaces 8a, 8b with the external flat surfaces 21a, 21b and one surface area established by the uppermost external surface 21f of the rod and the contact surface 41 of the fixation member 40. By means of this, a risk of slipping of the rod within the receiving part after tightening of the fixation member 40 is reduced, compared to a situation where only a line contact exists between the receiving part and the rod.

Because the angle β and the angle α are obtuse, a rotation of the rod 20 within the receiving part 3 when the fixation member is not yet fully screwed in is simplified, similar to a rod with circular cross-section.

Several modifications may be contemplated. While the rod is shown as a straight rod, also curved rods may be provided in the same manner. The external surfaces are then curved along the rod axis, which may then be defined infinitesimally for each cross-section of the rod. The flat external surfaces may also be provided only on portions of the rod in a lengthwise direction, while other portions of the rod may have a circular cross-section. Hence, the rod can be fixed along three contact areas when a portion of the rod having the flat external surfaces is placed into the receiving part 3, or it may be used as a rod having a circular cross-section when a portion with the circular cross-section is placed into the receiving part 3. The intermediate surfaces 22a, 22b ..., 22i can also be omitted. Thus, the rod can have a regular polygonal cross-section. The intermediate surfaces can also have another shape. The number of flat external surfaces is not limited to an uneven number, it can also be an even number.

The rod may also have cavities inside, such as a channel, i.e., the rod does not need to be a solid rod.

The fixation member 40 does not need to have a full flat bottom side. It is sufficient that one flat contact surface exists that cooperates with the uppermost flat external surface 21f of the rod.

Figure 12:
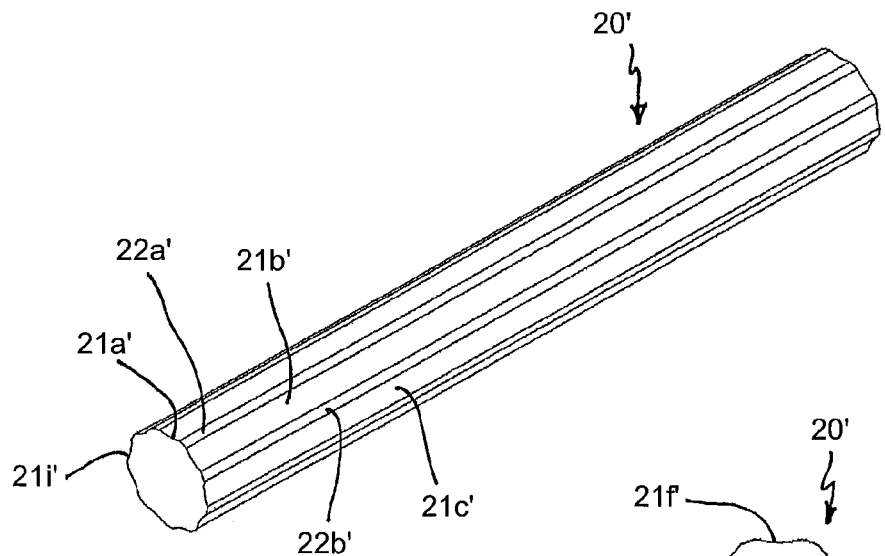
FIG. 12 shows a perspective view of a modification of the rod of the first embodiment.
Figure 13:
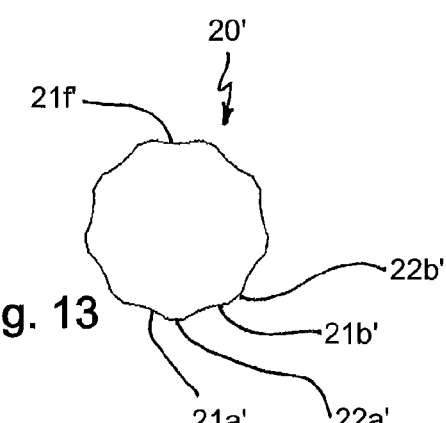
FIG. 13 shows a front view perpendicular to a rod axis of the rod of FIG. 12.
Figure 14:
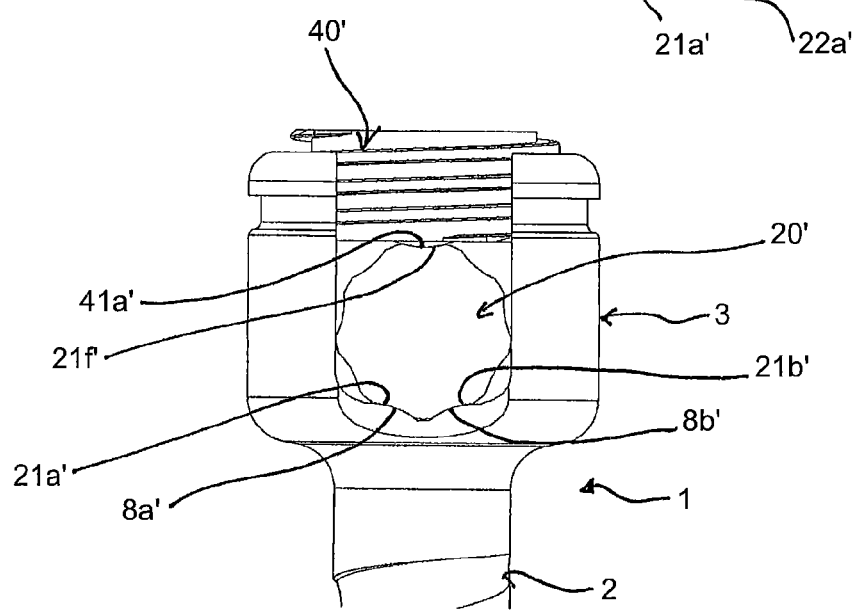
FIG. 14 shows a front view perpendicular to a rod axis of a modification of the first embodiment of the stabilization device.
Figure 15:
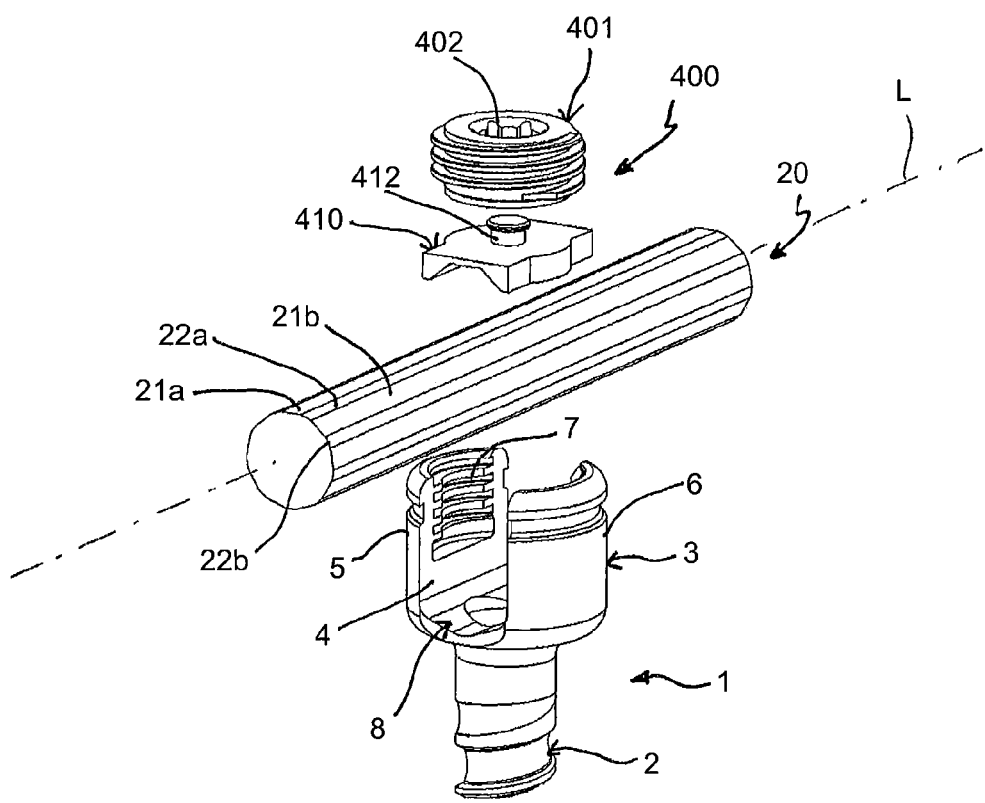
FIG. 15 shows a perspective exploded view of a stabilization device according to a second embodiment.
Figure 16:
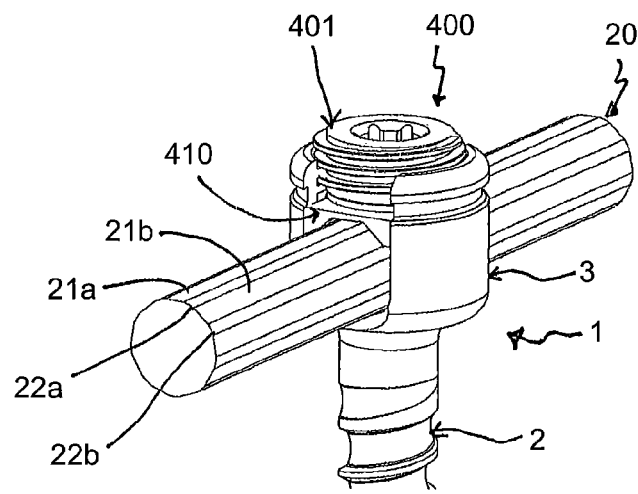
FIG. 16 shows a perspective view of the stabilization device of FIG. 15 in an assembled state.

Another modified embodiment of the stabilization device will be explained with reference to FIGS. 12 to 14. Parts that are identical or highly similar to the first embodiment will not be described again. The rod 20' includes a plurality of concave external surfaces 21a', 21b' ..., 21i'. The concave external surfaces 21a', 21b' ..., 21i' correspond to the flat external surfaces of the first embodiment. Also intermediate surfaces 22a', 22b', etc. that may be curved or flat can be present as in the first embodiment. The base 8' is also substantially V-shaped and includes two surfaces 8a', 8b' that are inclined with respect to each other and have convex projections in a cross-sectional view that fit into the concave external surfaces, for example, 21a', 21b', of the rod 20'. On the lower side of the fixation member 40', a cylindrical projection 41a' is provided that is shaped and sized so as to fit in the concave external surface 21f' of the rod 20' that is located on the uppermost side of the rod when the rod is inserted. The modified embodiment provides for an additional form-fit contribution to the rod fixation.

Referring to FIGS. 15 to 22, a second embodiment of the stabilization device will be described. The stabilization device according to the second embodiment differs from the stabilization device according to the first embodiment by the design of the fixation member. All other parts are identical or highly similar to those of the first embodiment and of the modification of the first embodiment. Hence, the rod according to the modification of the first embodiment as depicted in FIGS. 12 to 14, and all modifications thereof described above, can also be applied to the stabilization device according to the second embodiment.

Figure 17:
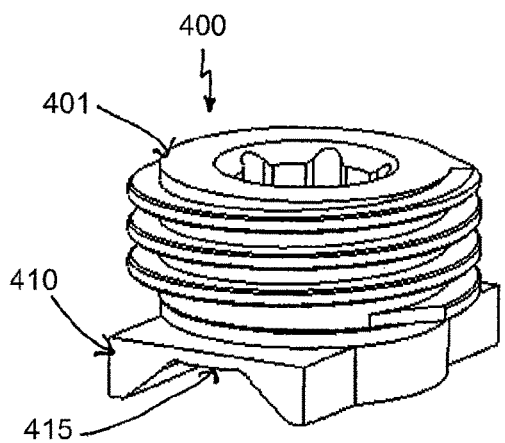
FIG. 17 shows a perspective view of a fixation member of the stabilization device according to FIGS. 15 and 16.
Figure 18:
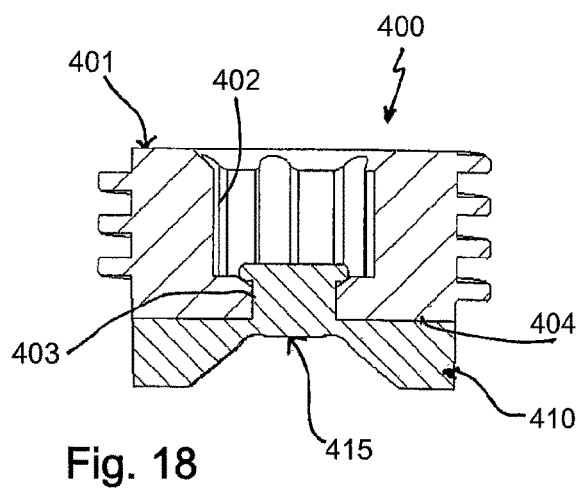
FIG. 18 shows a cross-sectional view of the fixation member of FIG. 17.
Figure 19:
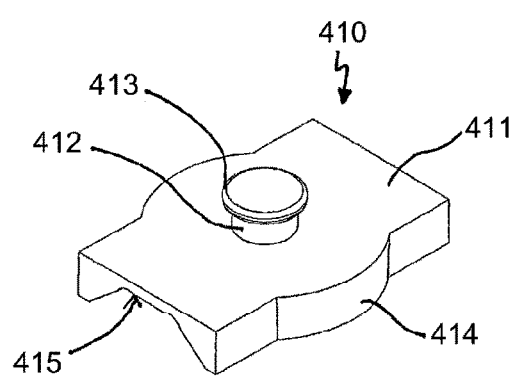
FIG. 19 shows a perspective view from the top of a second member of the fixation member of FIGS. 17 and 18.
Figure 20:
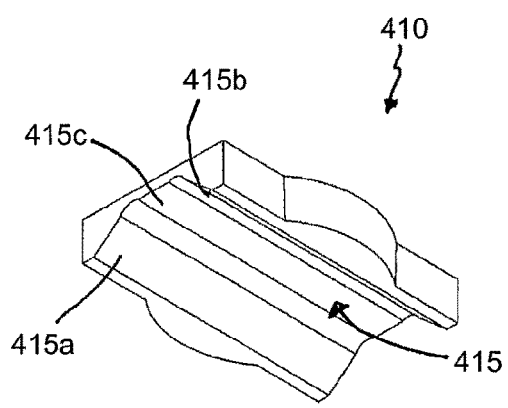
FIG. 20 shows a perspective view from the bottom of the second member of the fixation member shown in FIG. 19.
Figure 21:
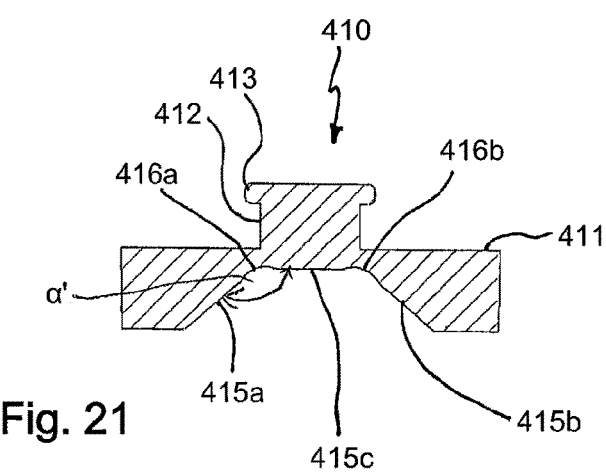
FIG. 21 shows a cross-sectional view of the second member of the fixation member shown in FIGS. 19 and 20.
Figure 22:
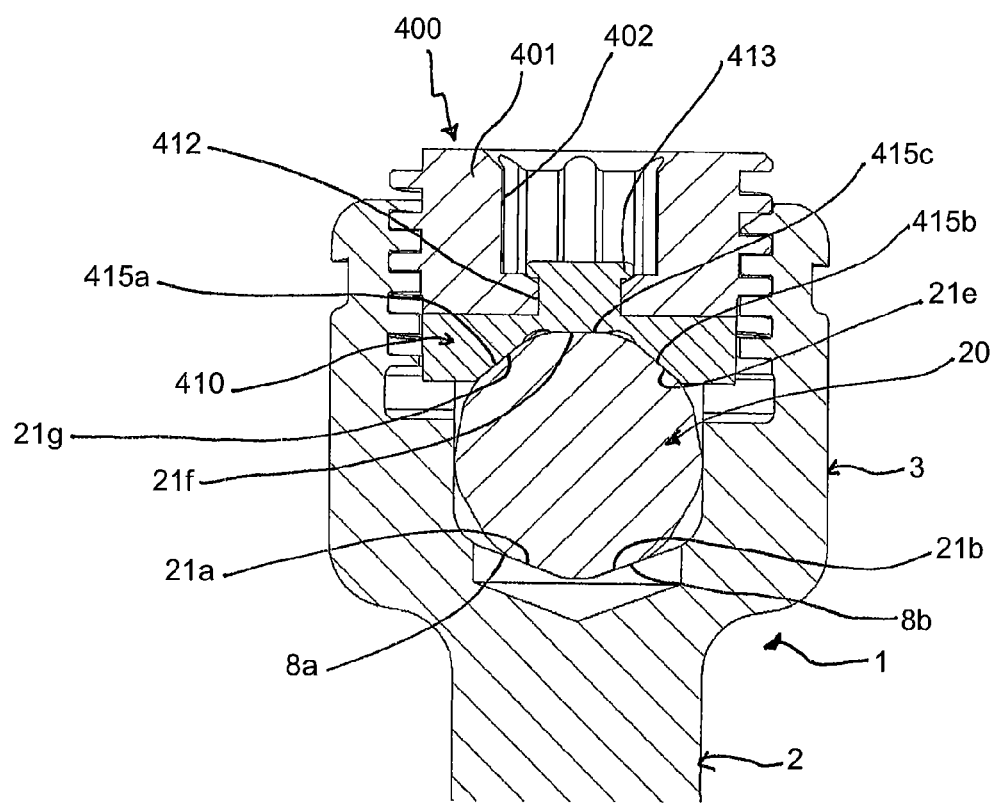
FIG. 22 shows a cross-sectional view of the stabilization device of FIGS. 15 and 16, the cross-section taken in a plane perpendicular to the rod axis.

The fixation member 400 includes a first fixation member 401 and a second fixation member 410 rotatably connected to the first fixation member 401. The first fixation member 401 is designed in the form of a set screw that is configured to cooperate with the internal thread provided on an inner wall of the legs 5, 6. The first fixation member 401 has a recess 402 configured to be engaged by a screwing-in tool at the side that is facing away from the second fixation member 410. As shown in FIG. 18, a coaxial bore 403 extends from the bottom of the recess 402 to the lower side 404 of the first fixation member 401. The lower side 404 may be formed as a flat surface. The second fixation member 410 has a substantially rectangular contour. A length of the second fixation member 410 corresponds substantially to a length of the channel formed by the recess 4 of the receiving part 3. A width of the second fixation member 410 is only slightly smaller than a width of the recess 4 of the receiving part 3, so that the second fixation member 410 may be inserted into the recess 4 and be guided therein. An upper surface 411 of the second fixation member 410 may be flat. In the center of the upper surface 411 a projection 412 is provided that may be cylindrical, and serves to rotationally engage the first fixation member 401, as shown in FIGS. 17 and 18. At a free end of the cylindrical projection 412, a rim 413 may be provided that holds the second fixation member 410 in the bore 403 of the first fixation member 401. At opposite long sides of the rectangular contour of the second fixation member 410, two cylinder segment-shaped bulges 414 may be provided that can engage the coaxial bore 7 in the receiving part 3.

A lower side of the second fixation member 410 that faces the rod 20 when the fixation member 400 is in the receiving part 3 defines a groove 415 that extends in the longitudinal direction of the second fixation member 410. The groove 415 has three flat surface portions 415a, 415b, and 415c extending in the longitudinal direction. The flat surfaces 415a, 415b, and 415c form a contour that is adapted to the contour of the outer surface of the rod, i.e., each of the flat surfaces forms a contact surface that engages a corresponding flat external surface of the rod 20. Hence, two consecutive contact surfaces 415a, 415c or 415c, 415b form an angle α' that corresponds to the angle β formed by the consecutive flat external surfaces of the rod 20.

Moreover, in a transverse direction of the groove 415 between the contact surfaces 415a, 415c, and 415b, intermediate rounded portions 416a, 416b may be formed.

With the second fixation member 410, additional contact surfaces 415a, 415b, 415c are provided that increase the clamping area, compared to the case where only one contact surface is provided by the fixation member.

In use, when the fixation member 400 is inserted into the channel provided by the recess 4 of the receiving part 3, the second fixation member 410 is moved downward by rotating the first fixation member 401, thereby engaging and clamping the rod 20.

It shall be understood that the second fixation member 410 may also be designed with five contact surfaces or more, thereby increasing the clamping area further. Also, an even number of contact surfaces, for example two, may be provided on the second fixation member 410, so that the number of external surfaces on the rod that cooperate with the contact surfaces may also be an even number. In this latter modified embodiment, the base in the receiving part may, for example, instead be flat so as to provide only one contact surface.

Referring to FIGS. 23 to 32, a third embodiment of the stabilization device will be described. The third embodiment includes a bone anchoring device that is designed as a polyaxial bone anchor including an outer locking ring. The rod 20 corresponds to the rod 20 of the first embodiment. It shall be understood that all modifications of the rod of the first embodiment can also be applied to the stabilization device of the third embodiment. In the same manner, the fixation member 400 of the second embodiment may be used. The polyaxial bone anchoring device 100 includes a bone anchoring element 101 with a shank 102 and a head 103 having a spherically-shaped outer surface portion. For example, the bone anchoring element 101 may be a bone screw with a threaded shank. The head 103 may have a recess 104 that serves for engagement with a tool, such as a driver. A receiving part 105 is provided for receiving the head 103 and connecting the bone anchoring element 101 via the head 103 to the rod 20. Furthermore, the fixation member 40" in the form of a set screw may be provided for fixing the rod 20 in the receiving part 105. Moreover, the bone anchoring device 100 includes a locking ring 107 for locking the head 103 in the receiving part 105.

The receiving part 105 has an upper end 5a and a lower end 5b. Adjacent to the upper end 5a, a rod receiving portion 150 is provided, and adjacent to the lower end 5b, a head receiving portion 160 is provided. The rod receiving portion 150 is substantially cylindrical and has a coaxial bore 151 that extends from the upper end 5a into the head receiving portion 160. The bore 151 has an internal thread in at least a region thereof for receiving the fixation member 40". A substantially U-shaped recess 152 that forms a channel for receiving the rod 20 extends from the upper end 5a to almost the beginning of the head receiving portion 160. At a distance from the upper end 5a, a groove or otherwise weakened section 153 is provided that allows breaking off of an upper portion of the receiving part 105 that serves as extended tabs. By means of the extended tabs, it is possible to manipulate the polyaxial bone anchoring device with an inserted rod 20 that is at a higher position compared to the final position at the bottom of the recess 152, so that, for example, a vertebra can be pulled against the rod 20.

At an outer surface of the rod receiving portion 150, an engagement structure for engagement with an instrument is provided. The engagement structure may include circumferentially extending ribs 154. The ribs 154 are arranged asymmetrically with respect to a plane including a central axis C of the receiving part 105 and a channel axis of the substantially U-shaped recess 152. Thereby, a rib-free surface 155 is also formed on each side of the U-shaped recess.

Beneath the ribs 154, a flat portion 156 is formed on an outer surface of the receiving part 105 for cooperating with the locking ring 107. Furthermore, two cut-outs 157 are formed at and extend downwardly from the bottom of the channel formed by the recess 152. A portion of the locking ring 107 can extend through the cut-outs 157.

The head receiving portion 160 has a substantially cap-like shape with a hollow substantially spherical interior portion 161 for pivotably receiving the head 3 therein. A plurality of slits 162 render the head receiving portion 160 flexible, so that when pressure is exerted onto the head receiving portion 160 by the locking ring 107, the head 3 can be clamped and finally locked.

As best shown in FIGS. 28 to 31, the locking ring 107 is designed to encompass the head receiving portion 160. The locking ring 107 has an internal substantially cylindrical section 170 that is configured to compress the head receiving portion 160 to lock the head 103 therein. Further, the locking ring 107 includes two opposite upstanding sections 171 that may serve for engagement with the receiving part 105 to preliminarily hold the locking ring 107 in an upper position. Moreover, two opposite projections 172 are provided at an upper side of the locking ring 107 that serve for supporting the rod 20. The opposite projections 172 each has an upper surface 173 with two contact surfaces 173a, 173b that are inclined with respect to each other and that form an angle corresponding to the angle of the flat external surfaces, for example, 21a, 21b, of the rod 20. In other words, the upper surfaces 173 of the projections 172 each forms a base for the rod 20. A circumferential width of the projections 172 is such that the projections 172 can extend through the cut-outs 157 of the rod receiving portion 150.

The locking ring 107 also includes two upstanding arms 175 that are asymmetrical with respect to a plane that extends through the central axis C and through the middle of the projections 172, in the same manner as the ribs 154 of the receiving portion 150 are arranged. At an upper end of the arms 175 an engagement structure 176 in the form of ribs and a groove is provided that is configured to be engaged by an instrument. In the assembled state, as depicted in FIG. 24, the engagement structure 176 is aligned with the ribs 154 on the receiving part 105, so that the rib-free surface portions 155 of the rod receiving portion 150 are exposed. This may facilitate the application of an instrument.

When the bone anchoring element 101 is inserted into the head receiving portion 160 and the locking ring 107 is around the head receiving portion 160, the projections 172 extend into the cut-outs 157 and provide a rod support surface 173.

Figure 32:
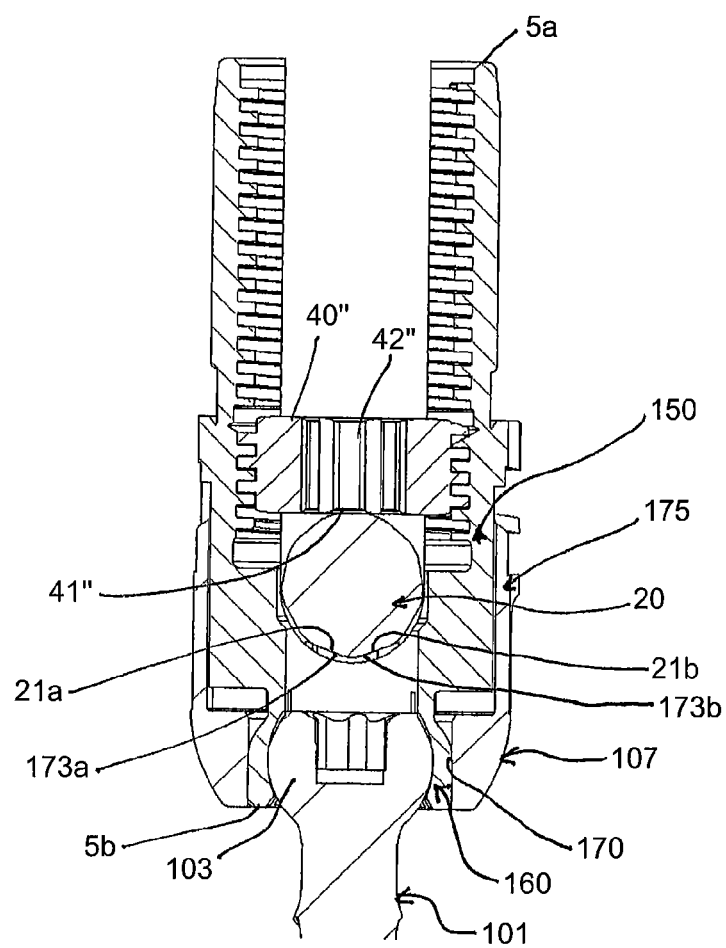
FIG. 32 shows a cross-sectional view of the stabilization device according to FIGS. 23 and 24, the cross-section taken in a plane perpendicular to the rod axis.

As shown in FIG. 32, the fixation member 40" may have a tool engagement recess 42" that extends fully through the fixation member 40". Hence, a lower contact surface 41" is ring-shaped.

In use, the receiving part 105 with the pre-assembled locking ring 107 is mounted onto the head 103 of the bone anchoring device 101, so that the head 103 is in the hollow interior 161. When the rod 20 is inserted it rests on the base provided by the rod support surface 173. When tightening the fixation member 40″, the rod 20 presses onto the rod support surface 173 thereby moving the locking ring 107 down. As a result, the head receiving portion 160 is compressed so that the head 103 is locked. The rod is clamped at three surface areas, two on the rod support surface and one on the fixation member 40″.

It shall be noted that the above monoaxial and polyaxial bone anchoring devices are only exemplary, and all other types of monoaxial and polyaxial bone anchoring devices can be used, as long as they provide for a rod support surface as discussed above. For example, polyaxial bone anchors with an inner compression member can be used in the same manner. The bone anchoring element and/or the shank can have any design that makes it suitable for anchoring in the bone or a vertebra.

The features of one embodiment or its modifications can be combined with those of another embodiment and its modifications, so that a variety of further embodiments can be provided without departing from the scope of the invention.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A stabilization device for bones or vertebrae comprising:
   a rod having a rod axis and comprising a rod portion with a plurality of distinct external surfaces that extend parallel to the rod axis, such that for a cross-section of the rod portion taken in a plane perpendicular to the rod axis, each of the distinct external surfaces is an outermost surface of the rod that faces at least partially radially outwardly and that extends circumferentially around the rod axis, and the distinct external surfaces are arranged at respective angles relative to one another and are separated from one another by respective intermediate surfaces, wherein a cross-sectional profile of each of the intermediate surfaces is convex while a cross-sectional profile of each of the distinct external surfaces is not convex; and
   a bone anchoring device comprising a receiving part having a channel for receiving the rod portion and a contact surface for supporting the rod portion, and a fixation member comprising a contact surface for fixing the rod in the channel;
   wherein when the rod portion is fixed in the channel with the fixation member, the contact surfaces of the receiving part and the fixation member together comprise surface portions that are shaped to correspond to at least three of the distinct external surfaces, such that the rod portion is clamped along the at least three distinct external surfaces, while at least one other one of the distinct external surfaces is spaced apart from the receiving part and the fixation member.

2. The stabilization device of claim 1, wherein the rod portion comprises at least five distinct external surfaces.

3. The stabilization device of claim 1, wherein the rod portion comprises an odd number of distinct external surfaces.

4. The stabilization device of claim 1, wherein each of the distinct external surfaces extends along a respective plane, and wherein none of the planes of the distinct external surfaces are parallel with one another.

5. The stabilization device of claim 1, wherein the distinct external surfaces are arranged in a rotationally symmetrical manner around the rod axis.

6. The stabilization device of claim 1, wherein two of the at least three distinct external surfaces of the rod portion are directly connected to opposite sides of one of the intermediate surfaces in a circumferential direction.

7. The stabilization device of claim 1, wherein a maximum outer width of the rod portion is smaller than an inner width of the channel of the receiving part.

8. The stabilization device of claim 1, wherein the distinct external surfaces of the rod portion are flat.

9. The stabilization device of claim 1, wherein the distinct external surfaces are concave.

10. The stabilization device of claim 1, wherein two of the distinct external surfaces that are directly connected to opposite sides of one of the intermediate surfaces in a circumferential direction form an obtuse angle with each other.

11. The stabilization device of claim 1, wherein the contact surface of the receiving part comprises two surface portions that form an angle with one another, and wherein the contact surface of the fixation member comprises a single surface portion.

12. The stabilization device of claim 1, wherein the contact surface of the fixation member comprises two or more surface portions.

13. The stabilization device of claim 1, wherein the fixation member comprises a first member configured to rotatably engage walls of the receiving part that define the channel for advancing in the channel, and a second member rotatably connected to the first member and comprising the contact surface of the fixation member.

14. The stabilization device of claim 13, wherein the second member has a substantially rectangular or square shape and a groove at a side opposite the first member that forms the contact surface of the fixation member.

15. The stabilization device of claim 1, wherein the contact surface of the receiving part is provided at a bottom of the channel.

16. The stabilization device of claim 1, wherein the receiving part of the bone anchoring device comprises a locking ring positionable around other portions of the receiving part to compress a head receiving portion of the receiving part, and wherein the contact surface of the receiving part is provided on the locking ring.

17. The stabilization device of claim 1, wherein the distinct external surfaces are formed on the entire rod.

18. The stabilization device of claim 1, wherein a cross-section of the contact surface of the receiving part is substantially V-shaped.

19. A method for connecting a stabilization device to a bone or vertebra, the stabilization device comprising a rod having a rod axis and comprising a rod portion with a plurality of distinct external surfaces that extend parallel to the rod axis, such that for a cross-section of the rod portion taken in a plane perpendicular to the rod axis, each of the distinct external surfaces is an outermost surface of the rod that faces at least partially radially outwardly and that extends circumferentially around the rod axis, and the distinct external surfaces are arranged at respective angles relative to one another and are separated from one another by respective intermediate surfaces, wherein a cross-sectional profile of each of the intermediate surfaces is convex while a cross-sectional profile of each of the distinct external surfaces is not convex, and a bone anchoring device comprising a shank, a receiving part connected to the shank and having a channel for receiving the rod portion and a contact surface for supporting the rod portion, and a fixation member comprising a contact surface for fixing the rod in the channel, the method comprising:

anchoring the shank to the bone or vertebra;

inserting the rod portion of the rod into the channel of the receiving part; and fixing the rod portion in the channel with the fixation member, wherein the contact surfaces of the receiving part and the fixation member together comprise surface portions that are shaped to correspond to at least three of the distinct external surfaces, such that the rod portion is clamped along the at least three distinct external surfaces, while at least one other one of the distinct external surfaces is spaced apart from the receiving part and the fixation member.

20. A stabilization device for bones or vertebrae comprising:

a rod having a rod axis and comprising a rod portion with a plurality of distinct external surfaces that extend parallel to the rod axis, such that in a plane perpendicular to the rod axis, a resulting cross-section of the rod portion has an odd number of distinct external surfaces arranged in a rotationally symmetrical manner around the rod axis;

a bone anchoring device comprising a receiving part having a channel for receiving the rod portion, a fixation member comprising a contact surface for fixing the rod in the channel, and a locking ring positionable around the receiving part, the locking ring having an upper side, a contact surface at the upper side for supporting the rod portion, and first and second upstanding sections at the upper side positionable away from channel, wherein the first upstanding section extends away from the upper side by a greater distance than the second upstanding section extends away from the upper side, and wherein the first and second upstanding sections both extend away from the upper side by different distances than the contact surface extends away from the upper side;

wherein when the rod portion is fixed in the channel with the fixation member, the contact surfaces of the receiving part and the fixation member together comprise surface portions that are shaped to correspond to at least three of the distinct external surfaces, such that the rod portion is clamped along the at least three distinct external surfaces.

21. The stabilization device of claim 20, wherein the resulting cross-section of the rod portion comprises at least five distinct external surfaces.

* * * * *

UNITED STATES PATENT AND TRADEMARK OFFICE
CERTIFICATE OF CORRECTION

PATENT NO. : 11,134,991 B2
APPLICATION NO. : 16/050753
DATED : October 5, 2021
INVENTOR(S) : Timo Biedermann et al.

It is certified that error appears in the above-identified patent and that said Letters Patent is hereby corrected as shown below:

In the Specification

Column 5, Line 9   Delete "poly-1-lactide" and insert -- poly-l-lactide --

Signed and Sealed this
Eighth Day of November, 2022

Katherine Kelly Vidal
*Director of the United States Patent and Trademark Office*